(12) United States Patent
Lankheet

(10) Patent No.: US 6,346,178 B1
(45) Date of Patent: Feb. 12, 2002

(54) SIMPLIFIED WIDE RANGE AIR FUEL RATIO SENSOR

(75) Inventor: Earl Wayne Lankheet, Grand Blanc, MI (US)

(73) Assignee: Delphi Technologies, Inc., Troy, MI (US)

(*) Notice: Subject to any disclaimer, the term of this patent is extended or adjusted under 35 U.S.C. 154(b) by 0 days.

(21) Appl. No.: 09/546,526

(22) Filed: Apr. 10, 2000

(51) Int. Cl.[7] .............................................. G01N 27/407
(52) U.S. Cl. ....................................... 204/424; 204/426
(58) Field of Search ................................. 204/421–429

(56) References Cited

U.S. PATENT DOCUMENTS

| | | | |
|---|---|---|---|
| 4,021,326 A | * | 5/1977 | Pollner et al. |
| 4,107,019 A | * | 8/1978 | Takao et al. |
| 4,177,112 A | * | 12/1979 | Suzuki et al. |
| 4,345,985 A | * | 8/1982 | Tohda et al. |
| 4,365,604 A | * | 12/1982 | Sone |
| 4,395,319 A | * | 7/1983 | Torisu et al. |
| 4,839,019 A | * | 6/1989 | Takahama et al. |

* cited by examiner

*Primary Examiner*—T. Tung
(74) *Attorney, Agent, or Firm*—Vincent A. Cichosz

(57) ABSTRACT

Herein described is an exhaust gas sensor that is used to detect gas concentration in a "lean only" exhaust stream. The gas sensor comprises a single cell within a dielectric substrate. The cell has an electrolyte with an inner and outer electrode disposed against opposite sides of the electrolyte. A porous protective layer is disposed against the outer electrode. Gases can enter and exit the galvanic cell through the porous protective layer. A voltage is applied across the electrodes, and ions are actively pumped out of the cell. The applied current can be used to determine a specific gas concentration in the exhaust stream.

9 Claims, 1 Drawing Sheet

SIMPLIFIED WIDE RANGE AIR FUEL RATIO SENSOR

BACKGROUND OF THE INVENTION

This invention relates generally to exhaust gas sensors, and specifically to exhaust oxygen sensors.

Oxygen sensors are used in a variety of applications that require qualitative and quantitative analysis of gases. Oxygen sensors have been used for many years in automotive vehicles to sense the presence of oxygen in exhaust gases. For example, sensors have been used to sense when an exhaust gas content switches from rich to lean or lean to rich. In automotive applications, the direct relationship between oxygen concentration in the exhaust gas and the air-to-fuel ratios of the fuel mixture supplied to the engine allows the oxygen sensor to provide oxygen concentration measurements for determination of optimum combustion conditions, for maximization of fuel economy, and for the management of exhaust emissions.

A conventional stoichiometric oxygen sensor typically consists of an electrochemical pumping cell and a reference cell. Sensors conventionally used in automotive applications use a yttria-stabilized, zirconia-based electrochemical galvanic cell operating in potentiometric mode to detect the relative amounts of oxygen present in an automobile engine's exhaust. When opposite surfaces of this galvanic cell are exposed to different oxygen partial pressures, an electromotive force is developed between the electrodes on the opposite surfaces of the zirconia ectrolyte, according to the Nernst equation:

$$E = \left(\frac{RT}{4F}\right)\ln\left(\frac{P_{O_2}^{ref}}{P_{O_2}}\right)$$

where:
E=electromotive force
R=universal gas constant
F=Faraday constant
T=absolute temperature of the gas
$P_{O_2}^{ref}$=oxygen partial pressure of the reference gas
$P_{O_2}$=oxygen partial pressure of the exhaust gas Due to the large difference in oxygen partial pressures between fuel rich and fuel lean exhaust conditions, the electromotive force changes sharply at the stoichiometric point, giving rise to the characteristic switching behavior of these sensors. Consequently, these potentiometric oxygen sensors indicate qualitatively whether the engine is operating fuel rich or fuel lean, without quantifying the actual air to fuel ratio of the exhaust mixture.

Further control of engine combustion can be obtained using amperometric mode exhaust sensors, in which oxygen is electrochemically pumped through an electrochemical cell by an applied voltage. A gas diffusion-limiting barrier creates a current limited output, the level of which is proportional to the oxygen content of the exhaust gas. These sensors conventionally consist of two or more electrochemical cells; one of these cells operates in potentiometric mode and serves as a reference cell, while another operates in amperometric mode and serves as an oxygen-pumping cell. This type of sensor, known as a wide range, lambda, or linear air/fuel ratio sensor, provides information beyond whether the exhaust gas is qualitatively rich or lean: it can quantitatively measure the air/fuel ratio of the exhaust gas.

One example of a conventional configuration for a gas sensor with a pumping cell and reference cell is shown in FIG. 1 generally at 10. The pumping cell comprises an electrolyte 12 disposed between an outer electrode 14 and an inner electrode 16.

The reference cell comprises a solid electrolyte 20 disposed between the inner electrode 16 and a reference electrode 22. Layers 24 of dielectric material, such as alumina, are used as a substrate into which the cell components are placed. One or more backing layers 26 are disposed against the reference electrode 22. Generally, a ground plane (not shown) and a heater (not shown) are disposed between these backing layers 26.

Conventional sensors can also have only one cell with a clean air reference. With a one cell arrangement, however, the clean air reference requires cumbersome sealing and porting complexity, and presents additional elements that are prone to failure during operation.

What is needed in the art is a simplified means for sensing exhaust gas without the need for the complexity of two cells or a single cell with an air reference.

BRIEF SUMMARY OF THE INVENTION

Disclosed herein is a device for sensing gas concentration in an exhaust flow comprising a dielectric substrate, a heater disposed within said substrate, a ground plane disposed within said substrate, and a cell consisting essentially of: an outer electrode disposed in electrical communication with an electrolyte, an inner electrode disposed in electrical communication with the electrolyte opposite to the outer electrode, and a protective layer disposed in fluid communication with the outer electrode, wherein the inner electrode is sealed such that gas contacting the inner electrode must first diffuse through the protective layer, the outer electrode, and the electrolyte.

The sensor provides a method for sensing the concentration of a gas in an exhaust stream, comprising: using a single cell disposed in a substrate, the cell consisting essentially of an outer electrode disposed in electrical communication with an electrolyte, an inner electrode disposed in electrical communication with the electrolyte opposite to the outer electrode, and a protective layer disposed in fluid communication with the outer electrode, wherein the inner electrode is sealed such that gas contacting the inner electrode must first diffuse through the protective layer, the outer electrode, and the electrolyte; applying a voltage to the cell, and measuring a current produced by the voltage, wherein the current is proportional to the concentration of the gas in the exhaust stream.

BRIEF DESCRIPTION OF THE DRAWINGS

The sensor will now be described, by way of example only, with reference to the accompanying drawings which are meant to be exemplary, not limiting, and wherein like elements are numbered alike, in which.

DETAILED DESCRIPTION OF THE INVENTION

Figure 1:
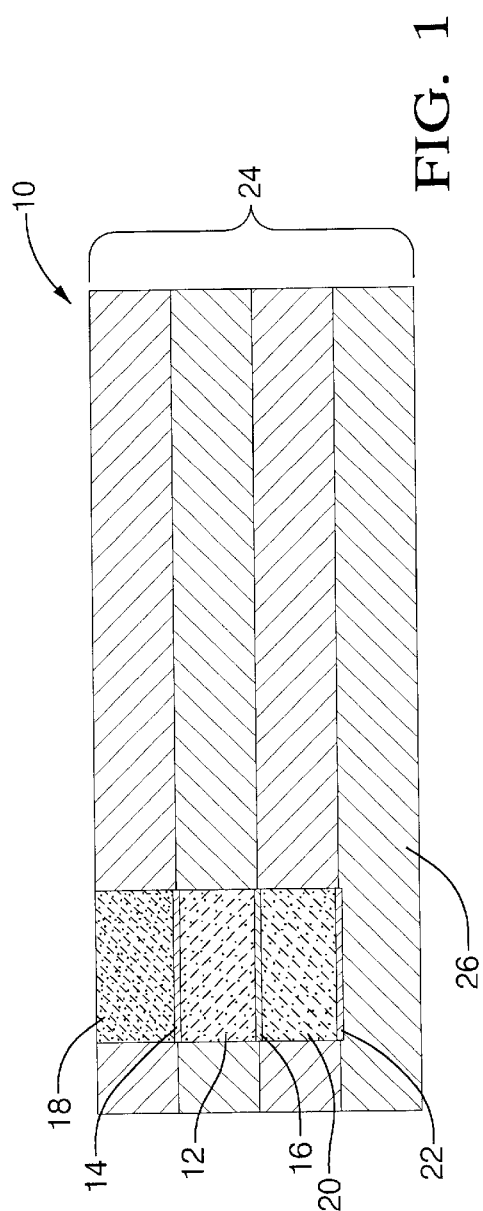
FIG. 1 is a cross sectional view of a prior art exhaust sensor.

The sensor is a single cell gas sensor that functions without the use of a second cell or an air reference. The sensor can be used in all conventional applications, and preferably in either a "lean only" or "rich only" application. In applications that are lean only or rich only, the measured exhaust gas never crosses the stoichiometric point. Since the main purpose of the reference cell is to determine which polarity should be applied to the pumping cell, a reference cell is not needed in a lean only or rich only application. Although the sensor will be described as an oxygen sensor, it is understood that the sensor could be a nitrous oxide sensor, hydrogen sensor, hydrocarbon sensor, or the like. Further, the sensor will be illustrated as a "lean only" sensor (e.g. for use in a diesel engine or the like), although it is understood that a "rich only" sensor can be arrived at by reversing the applied potential.

The sensor comprises an electrolyte disposed between an inner electrode and an outer electrode. A protective covering is disposed on the outer electrode opposite the electrolyte. The electrolyte, inner electrode, and outer electrode form a cell, and are preferably disposed adjacent to or within one or more layers of a dielectric substrate so that only the protective layer is exposed to the exhaust gas.

In one embodiment, the substrate layers are arranged in a parallel, planar configuration. The layers are initially fabricated as tape strips, and, after placement of the cell components, contacts, and other sensor components, the layers are fired or sintered to form a laminate sensor. The layers preferably comprise material having substantially similar coefficients of thermal expansion, shrinkage characteristics, and chemical compatibility, to at least minimize, if not eliminate, delamination and other processing problems. Typically these layers are composed of alumina or another dielectric material capable of inhibiting electrical communication and providing physical protection to the sensor components. These layers can be up to about 400 microns thick with a thickness of about 100 to about 200 microns preferred. The layers can be formed using ceramic tape casting methods or other methods such as plasma spray deposition techniques, screen printing, stenciling, film forming, and others conventionally used in the art. Any number of layers can be used, depending upon the desired structural integrity of the sensor and the thickness of each layer.

The electrolyte which can be disposed within or adjacent to a layer, can be made of oxygen conducting materials, including materials having a controlled porosity. Suitable materials include any material that is capable of permitting the electrochemical transfer of oxygen ions and the passage of oxygen molecules while inhibiting the physical passage of unwanted exhaust gases, has an ionic/total conductivity ratio of approximately unity, is compatible with the environment in which the sensor will be utilized, and is capable of acting as a barrier to diffusion. Possible electrolyte materials include conventional materials, e.g. metal oxides including zirconia and the like, such as yttria-stabilized zirconia, calcia-stabilized zirconia, magnesia-stabilized zirconia, silica-stabilized zirconia, and alumina-stabilized zirconia, and other conventional materials, as well as mixtures and alloys comprising at least one of the foregoing. Alternatively, the electrolyte can be a solid electrolyte having one or more holes, slits, or apertures therein, so as to enable the physical passage of exhaust gases. Typically, the electrolyte has a thickness of up to about 500 microns, with a thickness of approximately 25 micros to about 500 microns preferred. The electrolyte can be formed via many conventional processes including, but not limited to, die pressing, roll compaction, stenciling and screen printing. For improved process compatibility, it is preferred to utilize a tape process using known ceramic tape casting methods. The electrolyte is typically punched from a tape layer as an insert, and then inserted into a pre-punched hole in a substrate layer of alumina or other material.

The electrolyte is disposed between, and both in physical contact and ionic communication with an outer electrode and an inner electrode. Contacts are employed to provide an electrical connection for the electrodes. The electrodes can be any catalyst capable of ionizing oxygen, including, but not limited to, metal catalysts such as noble metals (platinum, palladium, rhodium, osmium, iridium, and ruthenium), and other metals, as well as alloys and combinations comprising at least one of the foregoing metals.

The electrodes should possess porosities sufficient to permit the diffusion of oxygen and exhaust gas molecules, and should have a thickness sufficient to attain the desired catalytic activity. Typically a porosity equal to or greater than the porosity of the electrolyte and a thickness of approximately 1.0 to about 25 microns can be employed, with a thickness of about 12 to about 18 microns generally preferred. As with the other sensor components, the electrodes can be formed using conventional techniques such as sputtering, chemical vapor deposition, screen printing, and stenciling, among others, with screen printing the electrodes onto appropriate tapes preferred due to simplicity, economy, and compatibility with the subsequent co-fired process.

A protective layer is preferably disposed in physical contact and ionic communication with the outer electrode. The protective layer can be any material that prevents erosion of the electrode, and smoothes the flow of exhaust gasses, and allows diffusion of oxygen but not unwanted exhaust gases into the cell, such as a ceramic, or porous zirconia, with porous zirconia preferred. (The porous zirconia can comprise any of the compositions listed for the electrolyte, above and others).

The geometry and size of the protective layer is based upon the size and geometry of the electrode and electrolyte. Consequently, the protective layer can be oval, circular, rectangular, multi-sided, etc. For example, the protective layer can be approximately cylindrical, with a thickness of about 25 to about 200 microns, and a width approximately equivalent to that of the electrolyte.

The sensor layer may optionally include a conventional lead gettering layer disposed between and in physical contact and ionic communication with the outer electrode and the protective layer, or within the protective layer itself. A lead gettering layer is preferably used when poisoning of the electrode by lead content in the exhaust stream is a concern.

In addition to the electrolyte, electrodes, protective layer, and lead gettering layer, the sensor can optionally include any conventional exhaust sensor component, including, but not limited to, substrate(s), a ground plane, a heater, contacts, and leads. The leads electrically connect various sensor components, e.g., electrodes, the ground plane, etc., to the contacts. The ground plane, which can be disposed between two of the substrate layers, inhibits sodium induced heater failure by drawing sodium ions out of the substrate (typically alumina) and retaining them. Meanwhile, the heater, serves to heat the sensor to a temperature at which gas sensing is optimized. As with the ground plane, the heater can be disposed between two substrate layers, typically at a thickness of about 5 to about 50 microns. The heater can be any conventional heater capable of maintaining the oxygen sensor at a sufficient temperature to facilitate the various electrochemical reactions therein, with a preferred operating temperature of about 700° C. to about 750° C. Typically the heater, comprises a metal (e.g., platinum, palladium and other metals), and/or a metal oxide (such as alumina and the like), as well as alloys comprising at least one of the foregoing.

Figure 2:
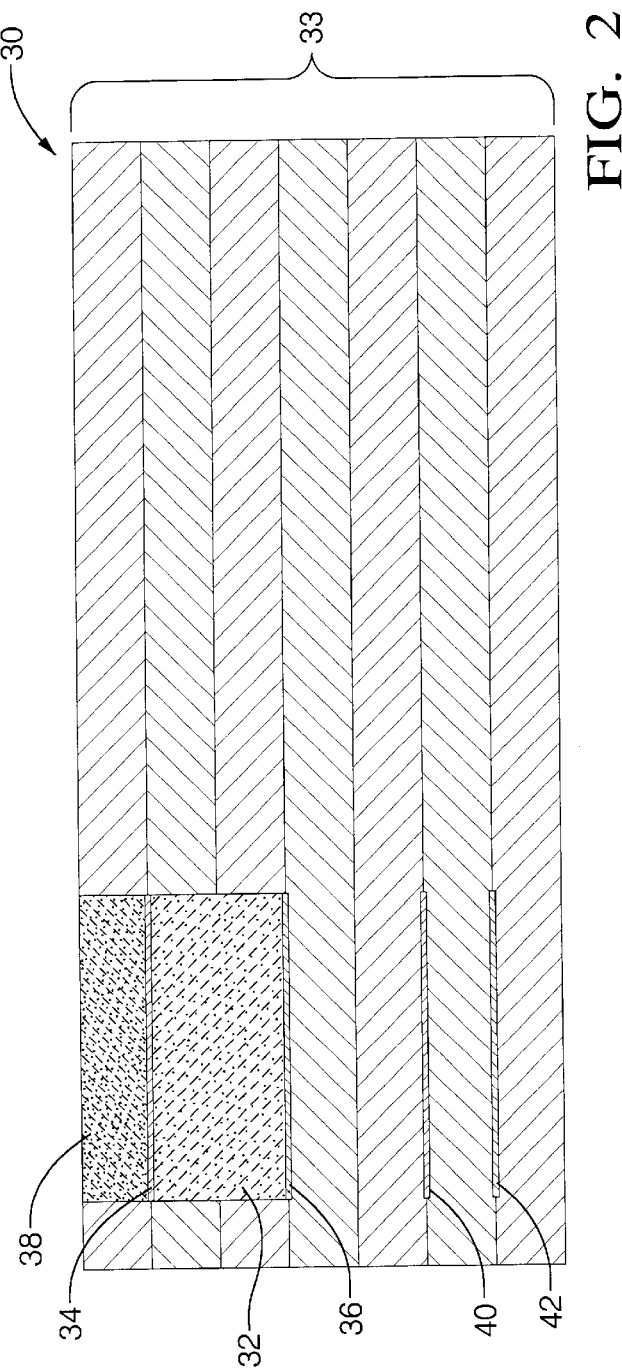
FIG. 2 is a cross sectional view of one embodiment of the exhaust sensor.

FIG. 2 shows the exhaust sensor generally at 30. The sensor comprises an electrolyte 32 disposed between and in physical contact and ionic communication with an inner electrode 36 and an outer electrode 34. A protective layer 38 is disposed against the outer electrode 34 opposite the electrolyte 32. The electrolyte 32, inner electrode 36, outer electrode 34, and protective layer 38 are disposed within layers 33 of a dielectric substrate so that only the protective layer 38 is exposed to the exterior of the substrate layers 33. That is, outside exhaust gases can only enter the sensor through the protective layer 38. Finally, a heater 40 and a ground plane 42 are disposed between the substrate layers 33. The protective layer 38, outer electrode 34, electrolyte 32, and inner electrode 36 can be any shape, with a generally circular shape typically preferred.

In operation, the sensor is positioned to expose the cell to an exhaust gas. When the sensor is exposed to an exhaust gas, oxygen that has not been consumed during combustion will enter the sensor through the protective layer 38 and diffuse through the diffusion barrier formed by the electrolyte 32. Oxygen reaching the inner electrode 36 will be ionized by an electrical potential applied between the electrodes 36, 34 with the outer electrode 34 being positive. With this applied potential, oxygen ions will be transferred or "pumped" through the solid structure of the electrolyte 32 from the inner electrode 36 to the outer electrode 34. The net effect of this oxygen transfer will be to create an oxygen concentration gradient across the electrolyte diffusion barrier 32 with the oxygen concentration at the inner electrode 36 being lower than the concentration at the outer electrode 34. The rate of oxygen diffusion through the electrolyte 32 diffusion barrier is directly proportional to the oxygen concentration differential. If the oxygen diffusion rate through the protective layer 38 is much higher than the oxygen diffusion rate through the electrolyte 32 diffusion barrier then the oxygen concentration at the outer electrode 34 will be very close to the exhaust gas oxygen concentration. If a sufficient voltage potential is applied to the ionic oxygen pumping cell, oxygen can be removed from the inner electrode 36 at a high enough rate to reduce the oxygen partial pressure at the inner electrode 36 to the about $10^{-4}$ to about $10^{-6}$ atmosphere range. In this case, the oxygen concentration at the inner electrode 36 can be considered to the effectively zero. The oxygen concentration differential across the electrolyte 32 then becomes equal to the exhaust gas oxygen concentration. The oxygen diffusion rate through the diffusion barrier then becomes limited and proportional to the exhaust gas oxygen concentration. To maintain the very low oxygen concentration at the inner electrode 36, the rate at which ionic oxygen is pumped away from the inner electrode 36 is limited and must be equal to the rate at which molecular oxygen is diffusing toward the inner electrode 36. The pump cell current is then proportional to the exhaust oxygen concentration when a limiting condition is established.

The basic operating equations are:

$$Q_{O_2} = D_{O_2}(P'_{O_2} - P''_{O_2});$$

and, $$I\alpha Q_{O_2} = D_{O_2}(P''_{O_2} - P''_{O_2})$$

Where:

$Q_{O_2}$=oxygen diffusion rate through the electrolyte diffusion barrier.

$D_{O_2}$=effective diffusion constant of electrolyte diffusion barrier.

$P'_{O_2}$=exhaust oxygen partial pressure.

$P''_{O_2}$=oxygen partial pressure at inner electrode.

I=electronic current supplied to oxygen pump cell.

If the sensor is operated in the current limiting mode so that $P''_{O_2}$ becomes effectively 0, then:

$$Q_{O_2} = D_{O_2}P'_{O_2} \text{ and } I\alpha D_{O_2}P'_{O_2}$$

The voltage to be applied to the pump cell can be described as:

$$V = IR_C + \left(\frac{RT}{4F}\right)\ln\left(\frac{P'_{O_2}}{P''_{O_2}}\right)$$

Where:

$R_C$=impedance of pumping cell.

R=universal gas constant.

T=absolute temperature.

F=Faraday's constant.

The value of the $IR_C$ term can be determined by monitoring pumping current (I) and measuring the pumping cell impedance. Periodic (e.g., several times a second) measurement of the pumping cell impedance can be accomplished by superimposing a small, high frequency (for example, about 30 kilohertz) voltage on the pump cell and measuring the resulting current pulse. The voltage level applied to the pump cell will be adjusted by the sensor's electronic controller to compensate for changes in the $IR_C$ term. The pump cell impedance ($R_C$) can be used as an indication of cell temperature and can be used as feedback to control power applied to the heater.

The value of the $$\left(\frac{RT}{4F}\right)\ln\left(\frac{P'_{O_2}}{P''_{O_2}}\right)$$

term in the pump cell voltage equation is established by the need to create a limiting current condition. This can only occur when $P'_{O_2}$ is equal to $10^{-6}$ atmosphere or less partial pressure of oxygen.

For typical operating conditions, this will occur when $$\left(\frac{RT}{4F}\right)\ln\left(\frac{P'_{O_2}}{P''_{O_2}}\right)$$

is about 0.5 volts.

The advantages of the sensor are significant. Since only one cell is used, and no air reference or reference cell is required, the wiring required to connect the reference cell electrodes to an external circuit are eliminated. Additionally, the control device that receives the signal from the sensor can be simpler, since reference measurements are not taken. Furthermore, overall sensor failure rates will be less for the sensor than the rates for conventional gas sensors since there are fewer components.

While preferred embodiments have been shown and described, various modifications and substitutions may be made thereto without departing from the spirit and scope of the invention. Accordingly, it is to be understood that the sensor has been described by way of illustration only, and such illustrations and embodiments as have been disclosed herein are not to be construed as limiting to the claims.

What is claimed is:

1. A device for sensing gas concentration in an exhaust flow, comprising:

a dielectric substrate;

a heater disposed in thermal and physical communication with the substrate; and a single cell disposed in physical communication with the substrate, the cell consisting essentially of an outer electrode disposed in electrical communication with an electrolyte, an inner electrode disposed in electrical communication with the electrolyte opposite to the outer electrode, and a protective layer disposed in fluid communication with the outer electrode, and electrical leads electrically connecting the inner electrode and the outer electrode to an electrical device, wherein the inner electrode is sealed such that gas contacting the inner electrode must first diffuse through the protective layer, the outer electrode, and the electrolyte.

2. The device of claim 1, wherein the electrolyte comprises zirconia.

3. The device of claim 1, wherein the protective layer comprises zirconia.

4. The device of claim 1, wherein the electrolyte has a thickness of less than about 500 microns.

5. The device of claim 4, wherein the electrolyte has a thickness of about 25 to about 500 microns.

6. The device of claim 1, wherein the outer electrode and the inner electrode have a thickness of about 1 to about 25 microns.

7. The device of claim 6, wherein the outer and the inner electrode have a thickness of about 12 to about 18 microns.

8. The device of claim 1, wherein the protective layer has a thickness of about 25 to about 200 microns.

9. The device of claim 1, wherein the cell is disposed within an aperture disposed through at least a portion of the substrate.

* * * * *